(12) United States Patent
Moreno et al.

(10) Patent No.: US 7,892,170 B2
(45) Date of Patent: Feb. 22, 2011

(54) SURGICAL ACCESS DEVICE AND MANUFACTURE THEREOF

(75) Inventors: Miguel Moreno, Salinas, PR (US); Richard D. Gresham, Guilford, CT (US); Thomas Wenchell, Durham, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 759 days.

(21) Appl. No.: 10/967,056

(22) Filed: Oct. 15, 2004

(65) Prior Publication Data

US 2005/0192608 A1    Sep. 1, 2005

Related U.S. Application Data

(60) Provisional application No. 60/512,548, filed on Oct. 17, 2003.

(51) Int. Cl.
    *A61B 1/00* (2006.01)
(52) U.S. Cl. ...................................................... 600/184
(58) Field of Classification Search ................ 606/108, 606/185; 604/164.1, 164.03, 164.01, 164.11, 604/264, 338, 540, 543, 164.04, 164.07; 600/184, 585, 20
    See application file for complete search history.

(56) References Cited

U.S. PATENT DOCUMENTS

| | | | |
|---|---|---|---|
| 1,361,758 A * | 12/1920 | Ewald | ......................... 285/248 |
| 4,490,136 A * | 12/1984 | Ekbladh et al. | ................ 604/22 |
| 4,772,266 A | 9/1988 | Groshong | |
| 4,899,729 A | 2/1990 | Gill et al. | |
| 4,921,479 A | 5/1990 | Grayzel | |
| 4,954,126 A | 9/1990 | Wallstén | |
| 5,066,285 A | 11/1991 | Hillstead | |
| 5,085,645 A * | 2/1992 | Purdy et al. | ............. 604/167.03 |
| 5,139,511 A | 8/1992 | Gill et al. | |
| 5,158,545 A | 10/1992 | Trudell et al. | |
| 5,178,133 A * | 1/1993 | Pena | ........................... 600/203 |
| 5,183,464 A | 2/1993 | Dubrul et al. | |
| 5,234,425 A | 8/1993 | Fogarty et al. | |
| 5,250,033 A | 10/1993 | Evans et al. | |
| 5,256,150 A | 10/1993 | Quiachon et al. | |
| 5,318,588 A | 6/1994 | Horzewski et al. | |
| 5,320,611 A | 6/1994 | Bonutti et al. | |
| 5,395,341 A | 3/1995 | Slater | |
| 5,423,776 A * | 6/1995 | Haindl | ........................ 604/533 |
| 5,423,849 A | 6/1995 | Engelson et al. | |
| 5,431,676 A | 7/1995 | Dubrul et al. | |
| 5,441,504 A | 8/1995 | Pohndorf et al. | |
| 5,443,484 A * | 8/1995 | Kirsch et al. | ............ 604/164.04 |
| 5,454,790 A | 10/1995 | Dubrul | |
| 5,460,170 A * | 10/1995 | Hammerslag | ................ 600/201 |
| 5,499,975 A | 3/1996 | Cope et al. | |
| 5,573,517 A | 11/1996 | Bonutti et al. | |

(Continued)

FOREIGN PATENT DOCUMENTS

WO     WO 03011154     2/2003

*Primary Examiner*—Anhtuan T Nguyen
*Assistant Examiner*—Thomas McEvoy

(57) ABSTRACT

A surgical access system includes a tubular member defining a longitudinal axis and having an axial lumen. The tubular member includes a braided material adapted to expand from a first initial condition having a first cross-sectional dimension to a second expanded condition having a second-cross sectional dimension greater than the first cross-sectional dimension. The tubular member defines an oblique end surface. An access housing is mounted to the tubular member. The access housing is dimensioned for engagement by the user. A process for manufacturing a surgical access device is also disclosed.

12 Claims, 6 Drawing Sheets

U.S. PATENT DOCUMENTS

| | | | |
|---|---|---|---|
| 5,626,602 A | 5/1997 | Gianotti et al. | |
| 5,630,822 A | 5/1997 | Hermann et al. | |
| 5,660,186 A * | 8/1997 | Bachir | 600/562 |
| 5,688,246 A | 11/1997 | Waitz et al. | |
| 5,746,720 A * | 5/1998 | Stouder, Jr. | 604/117 |
| 5,782,807 A | 7/1998 | Falvai et al. | |
| 5,814,058 A | 9/1998 | Carlson et al. | |
| 5,814,073 A | 9/1998 | Bonutti | |
| 5,827,227 A | 10/1998 | DeLago | |
| 5,827,319 A * | 10/1998 | Carlson et al. | 606/191 |
| 5,836,913 A | 11/1998 | Orth et al. | |
| 5,944,691 A | 8/1999 | Querns et al. | |
| 5,957,902 A | 9/1999 | Teves | |
| 5,961,499 A | 10/1999 | Bonutti et al. | |
| 5,984,957 A | 11/1999 | Laptewicz, Jr. et al. | |
| 6,019,776 A * | 2/2000 | Preissman et al. | 606/185 |
| 6,056,772 A | 5/2000 | Bonutti | |
| 6,080,174 A | 6/2000 | Dubrul et al. | |
| 6,090,072 A | 7/2000 | Kratoska | |
| 6,159,179 A | 12/2000 | Simonson | |
| 6,162,236 A * | 12/2000 | Osada | 606/185 |
| 6,183,443 B1 | 2/2001 | Kratoska et al. | |
| 6,221,064 B1 * | 4/2001 | Nadal | 604/533 |
| 6,228,052 B1 | 5/2001 | Pohndorf | |
| 6,245,052 B1 | 6/2001 | Orth et al. | |
| 6,293,909 B1 | 9/2001 | Chu et al. | |
| 6,325,812 B1 | 12/2001 | Dubrul et al. | |
| 6,338,730 B1 | 1/2002 | Bonutti et al. | |
| 6,358,238 B1 | 3/2002 | Sherry | |
| 6,364,897 B1 | 4/2002 | Bonutti | |
| 6,387,095 B1 | 5/2002 | Kennett et al. | |
| 6,428,556 B1 | 8/2002 | Chin | |
| 6,494,893 B2 | 12/2002 | Dubrul et al. | |
| 6,589,225 B2 | 7/2003 | Orth et al. | |
| 6,589,262 B1 | 7/2003 | Honebrink et al. | |
| 6,613,038 B2 | 9/2003 | Bonutti et al. | |
| 6,669,681 B2 * | 12/2003 | Dudar et al. | 604/533 |
| 2003/0055446 A1 | 3/2003 | Seward et al. | |
| 2003/0176771 A1 * | 9/2003 | Pulford et al. | 600/208 |
| 2003/0216770 A1 * | 11/2003 | Persidsky et al. | 606/191 |

* cited by examiner

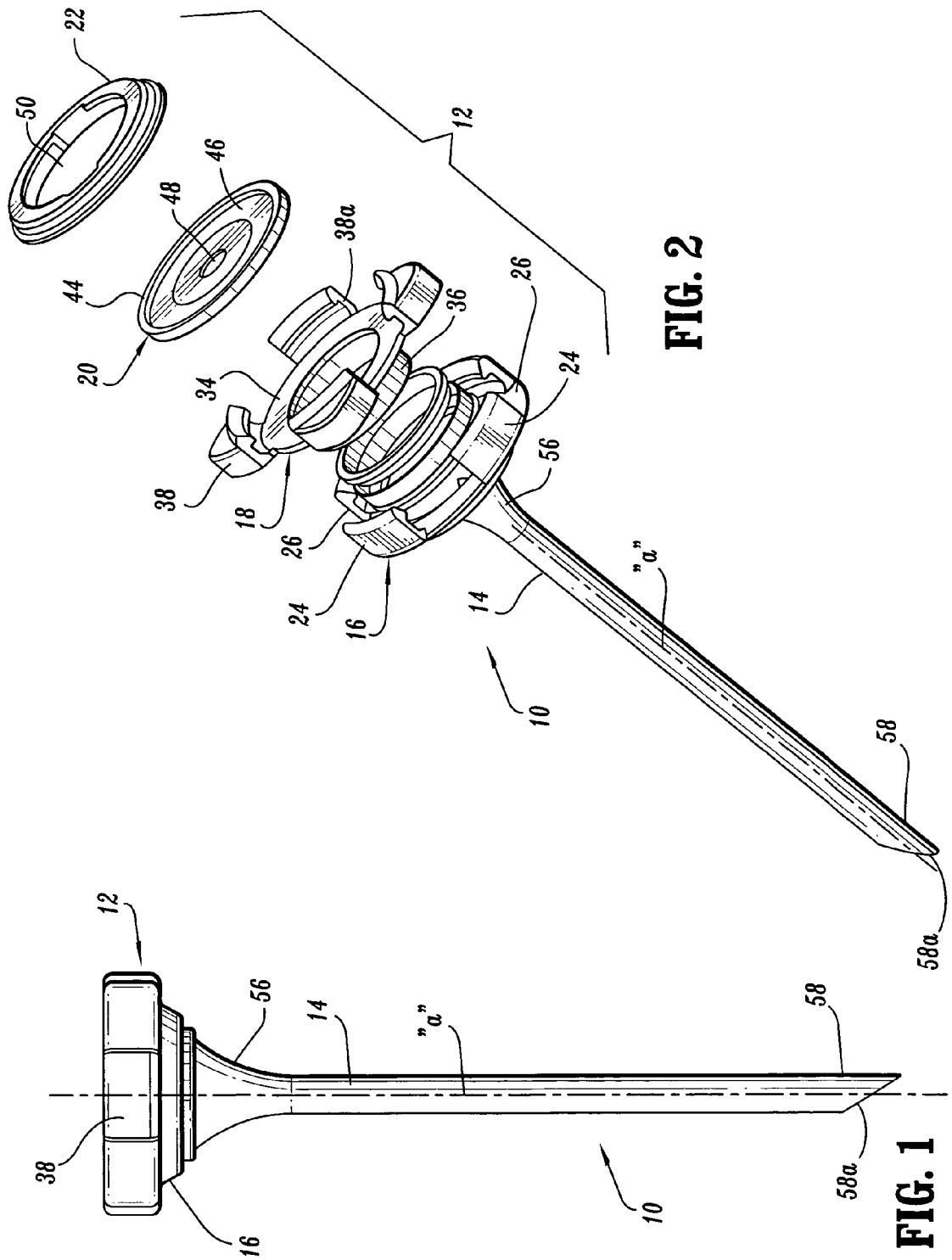

US 7,892,170 B2

SURGICAL ACCESS DEVICE AND MANUFACTURE THEREOF

CROSS-REFERENCE TO RELATED APPLICATIONS

This application claims the benefit of priority of U.S. Provisional Patent Application Ser. No. 60/512,548, filed on Oct. 17, 2003, the entire disclosure of which is hereby incorporated by reference herein.

BACKGROUND

1. Field of the Disclosure

The present disclosure relates generally to an apparatus and method for providing percutaneous access to an internal operative site during a surgical procedure. More particularly, the present invention relates to an access system which can be percutaneously introduced in a narrow diameter configuration and thereafter radially expanded to accommodate passage of larger diameter surgical instruments. The present disclosure is further related to a process of manufacture of the access system.

2. Description of the Prior Art

Minimally invasive surgical procedures involve percutaneously accessing an internal surgical site with small-diameter access tubes (typically 5 to 12 mm), usually referred to as trocars, which penetrate the skin and permit access to the desired surgical site. A viewing scope is introduced through one such trocar, and the surgeon operates using instruments introduced through other appropriately placed trocars while viewing the operative site on a video monitor connected to the viewing scope. The surgeon is thus able to perform a wide variety of surgical procedures requiring only several 5 to 12 mm punctures at the surgical site. Patient trauma and recovery time are thus greatly reduced.

Minimally invasive surgical procedures include laparoscopic procedures which involve the insufflation of the patient's abdominal region to raise the abdominal wall and create sufficient operating space to perform a desired procedure. The trocars used in laparoscopic procedures incorporate a valve to permit passage of the scope or surgical instruments while inhibiting leakage of the insufflating gas. It has also been proposed to perform laparoscopic procedures by mechanically expanding the abdomen rather than using insufflation.

Other minimally invasive surgical procedures include thoracoscopic procedures performed in the region of the chest, arthroscopic procedures performed in body joints, particularly the knee, gynecological laparoscopic procedures, and endoscopic surgical procedures performed in various regions of the body, typically with a flexible scope. These latter procedures do not normally employ pressurization and the trocars used generally do not include pressure valves at their proximal ends.

The design of suitable trocars must fulfill many requirements, particularly for those used in laparoscopic procedures in a pressurized environment. Trocars should be introducible within the patient with minimum trauma and with minimum risk of injury to internal organs. The trocars used in laparoscopic procedures should be readily sealable to inhibit the leakage of gas from the abdomen, and, in particular, should be designed to inhibit leakage in the region surrounding the external periphery of the trocar which passes through the abdominal wall. It is further desirable that trocars incorporate structure for anchoring within the percutaneous passage, and it would be particularly desirable if a single trocar could accommodate instruments having a wide variety of cross-sectional shapes and sizes.

Commonly assigned U.S. Pat. No. 5,431,676 to Dubrul et al., the contents of which are incorporated herein by reference in its entirety, discloses in certain embodiments an access system incorporating an elongate dilation member and an expansion member receivable within an axial lumen of the trocar. The dilation member includes a tubular braid which is radially expandable from a small diameter configuration to a large diameter configuration. A removable sheath may cover the braid. In use, the dilation member is percutaneously introduced to a target site within a patient's body, e.g., within the abdomen of the patient. The expansion member is thereafter introduced within the dilation member to break the sheath and radially expand the tubular braid to provide a desired diameter access lumen. The device disclosed in Dubrul '676 has proven to be highly effective in conjunction with laparoscopic and other minimally invasive surgical procedures. However, it would be desirable to include features facilitating the insertion of the expansion member and for facilitating insertion of the dilation member into the body. In addition, efficient and effective methods of manufacturing the process system are desirable.

SUMMARY

Accordingly, the present disclosure relates to an improved apparatus, system and method for forming and enlarging percutaneous penetrations into target locations within a patient's body. In one preferred embodiment, a surgical access system includes a tubular member defining a longitudinal axis and having an axial lumen. The tubular member comprises a braided material adapted to expand from a first initial condition having a first cross-sectional dimension to a second expanded condition having a second-cross sectional dimension greater than the first cross-sectional dimension. The tubular member defines an oblique end surface. An access housing is mounted to the tubular braid and is dimensioned for engagement by the user.

The tubular member includes a mounting element mounted therewithin. The mounting element facilitates attachment of the tubular member to the access housing. The mounting element is dimensioned to frictionally engage an internal wall portion of the tubular member. The access housing may include a base and a cover mountable to the base. The base is adapted to receive a proximal end of the tubular member and the mounting element is engageable with a locking shelf of the base. The access housing may further include a seal element mounted within the base and defining an aperture for sealed reception of an elongate object.

The surgical access system may further include a dilator member. The dilator member is adapted for insertion within the tubular braid to expand the tubular braid between the first and second conditions. The dilator member is preferably a cannula.

A process for manufacturing a surgical access device, includes the steps of:

providing a tubular braid, the braid defining a longitudinal axis and having an axial lumen, the tubular braid adapted to expand from a first initial condition having a first cross-sectional dimension to a second expanded condition having a second-cross sectional dimension greater than the first cross-sectional dimension;

positioning an elastomer layer over at least a portion of the tubular braid;

subjecting the elastomer layer and the tubular braid to heat to thereby form an elastomer-braid subassembly;

creating a flared end portion of the elastomer-braid subassembly;

inserting the elastomer-braid subassembly within an access housing base; and securing an access housing hub to the access housing base whereby at least the flared end portion of the elastomer-braid subassembly is secured within the access housing hub and the access housing base.

BRIEF DESCRIPTION OF THE DRAWINGS

Preferred embodiments of the present disclosure will be better appreciated by reference to the drawings wherein:

FIG. 1 is an elevational view of the access apparatus in accordance with an embodiment of the present disclosure;

FIG. 2 is a an exploded perspective view of the access apparatus in accordance with the embodiment of FIG. 1 with parts separated;

DETAILED DESCRIPTION OF THE PREFERRED EMBODIMENTS

Figures 3, 4:
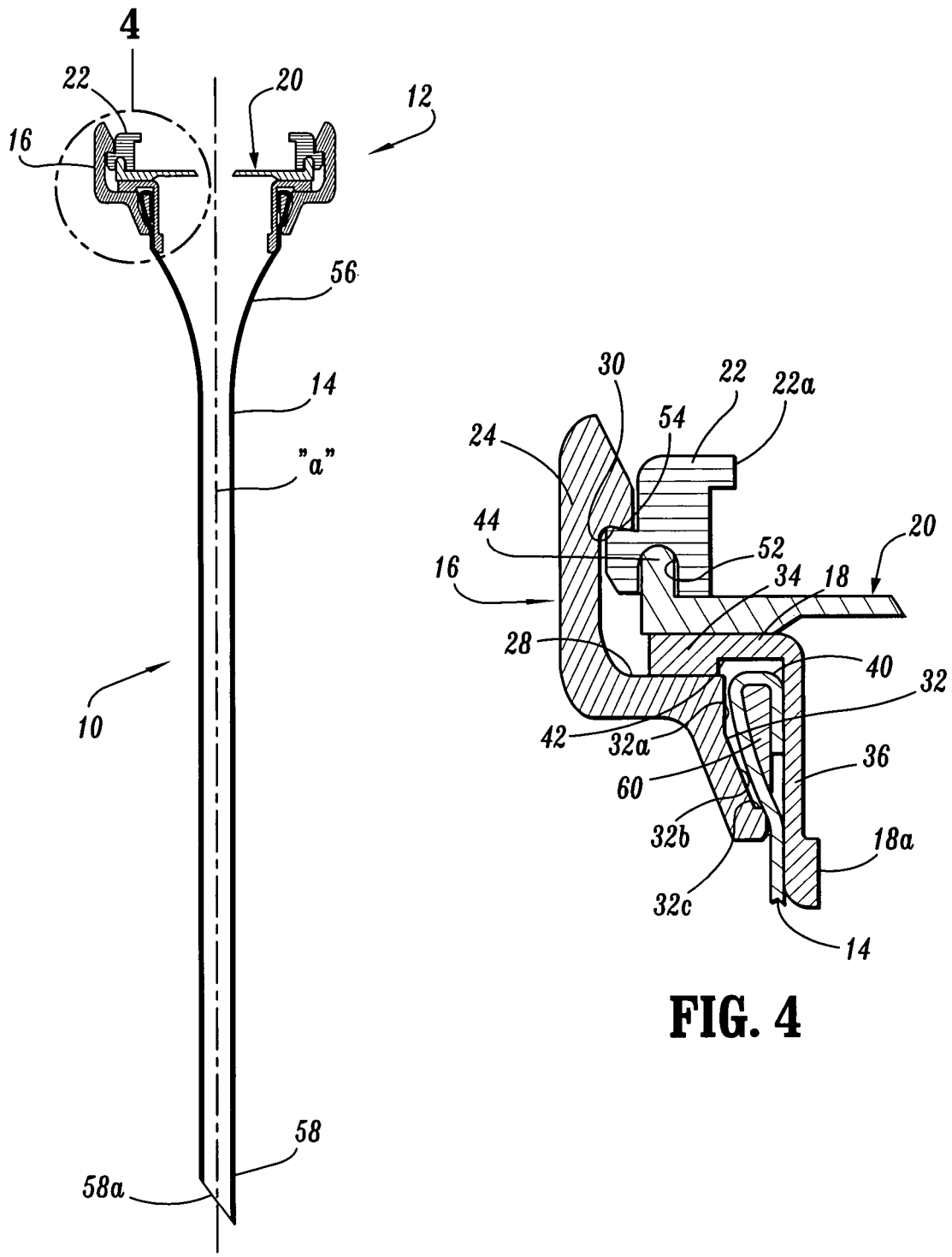
FIG. 3 is a cross-sectional view of the access apparatus in accordance with the embodiment of FIGS. 1-2.
FIG. 4 is an enlarged cross-sectional view of the proximal end of the access apparatus in accordance with the embodiment of FIGS. 1-3.

The principles of the present disclosure are applicable to a variety of surgical access devices adapted for permitting percutaneous access to a target site. These access devices include, but are not limited to, trocars and/or cannulas, catheters, hand access devices, scopes, etc. The present disclosure is contemplated for use in various surgical procedures including, e.g., laparoscopic, arthroscopic, thoracic, etc.

The following discussion will initially focus on the structure and components of the novel access device followed by a preferred method of manufacture thereof. A method of use of the apparatus will be subsequently discussed.

In the following description, as is traditional, the term "proximal" will refer to the portion of the instrument closest to the operator while the term "distal" refers to the portion of the instrument most remote from the operator.

Referring now to the drawings wherein like reference numerals identify similar or like elements throughout the several views, FIGS. 1-4 illustrate the novel access apparatus in accordance with the principles of the present disclosure. Access device 10 generally includes housing 12 and elongate member 14 extending from the housing 12. Housing 12 and elongate member 14 define a longitudinal axis "a" which extends through and along the length of the device 10.

With continued reference to FIGS. 1-4, housing 12 includes several components, which, when assembled, define a structure advantageously dimensioned to be held by the surgeon. These components include base 16, hub 18, seal 20 and cover 22. Base 16 defines an outer wall 24 having a plurality of spaced recesses 26 therein. Recesses 26 are generally rectangular in configuration as shown. The interior of base 16 has transverse ledge 28 upon which hub 18 rests and locking shelf 30 adjacent the proximal end of the base 16. Base 16 defines a distal tapered portion 32 which tapers inwardly relative to the longitudinal axis "a". In the preferred embodiment, tapered portion 32 incorporates a pair of intersecting surfaces 32a, 32b and a transverse shelf 32c. Tapered portion 32 functions in securing elongate member 14 to base 16 as will be discussed.

Hub 18 of housing 12 includes disc-shaped portion 34 and annular wall 36 extending distally from the disc-shaped portion 34. Disc-shaped portion 34 has a plurality of vertical locks 38 extending upwardly from the disc-shaped portion 34. Vertical locks 38 are received within correspondingly positioned and dimensioned recesses 26 of base 16 in the assembled condition of housing 12. Vertical locks 38 each have an internal locking shelf 38a, which in combination with shelves 30 of the base 16 defines a continuous locking shelf when hub 18 is assembled within the base 16. Annular wall 36 of hub 18 is generally continuous and defines a diameter which is less than the effective internal diameter of base 16, and/or the effective diameter of the proximal end of elongate member 14. Annular wall 36 is received within base 16 and elongate member 14 upon assembly of the device 10. Hub 18 further includes a resilient seal or o-ring 40 which is accommodated within groove 42 disposed on the underside of the hub 18. O-ring 40 is adapted to form a gas-tight seal between hub 18 and base 16.

With continued reference to FIGS. 1-4, seal 20 includes an outer circumferential wall 44 and an inner seal portion 46 extending radially inwardly relative to the longitudinal axis "a". Inner seal portion 46 defines central aperture 48 which is dimensioned for passage of an object, e.g., a surgical instrument, guide wire, catheter or the hand of a surgeon. Seal 20 may be fabricated from any elastomeric material suitable for its intended purpose. A friction resisting coating may be applied to seal 20. Other valve types are also contemplated including zero-closure valves, slit valves, septum valves, double-slit valves, inflatable bladders, foam or gel valve arrangements, etc.

Cover 22 has a general annular shape as shown defining a central opening 50 for permitting passage of the object. Cover 22 includes circumferential recess 52 on its underside or distal end face which accommodates outer circumferential wall 44 of seal 20. The peripheral area of cover 22 defines a ledge or shelf 54 which, in the assembled condition, engages locking shelf 30 of base 16 and/or locking shelf 38a of vertical locks 38 of hub 18 in snap relation therewith to thereby secure the remaining components of housing 12 within the base 16. Other mechanical arrangements for securing cover 22 to base 16 are also envisioned including, e.g., a screw thread arrangement, bayonet coupling, etc.

The components of housing 12 may be fabricated from any suitable generally rigid material (notwithstanding seal) including stainless steel, titanium or a rigid polymeric material. The components of housing 12 may be fabricated from any suitable medical grade material.

Referring still to FIGS. 1-4, elongate member 14 will be discussed. Elongate member 14 defines a general tubular shape having proximal end 56 and distal end 58. Proximal end 56 is flared radially outwardly in a proximal direction and secured to housing 12. Distal end 58 includes an inclined surface 58a obliquely arranged relative to the longitudinal axis. This surface 58a facilitates passage of elongate member 14 through the tissue. Tubular elongate member 14 may be fabricated from any material which is capable of receiving the assembly of a cannula, dilator, or surgical instrument and capable of radial expansion of the elongate member 14. The materials are desirably medical grade materials including polymers and metals. In an exemplary embodiment, elongate member 14 includes a braided material of inelastic filaments covered by an elastomeric membrane of, e.g., urethane, or any elastomeric material or as generally disclosed in commonly assigned U.S. Pat. Nos. 5,431,676 and 6,245,052, the contents of each being incorporated herein by reference. It is also envisioned that a polyethylene sheath may be assembled over elongate member 14. The elongate member may comprise an elastomeric member or members without the braided material. Embodiments may include a material incorporating filaments, where the filaments may be elastic, inelastic, monofilaments, multifilaments, braided, woven, knitted or non-woven materials. The elongate member may comprise a braided, woven, knitted or non-woven material with or without an elastomeric membrane.

With particular reference to FIG. 4, elongate member 14 has a mounting element or ring 60 which is anchored within elongate member 14 adjacent proximal end 56. Mounting ring 60 is preferably retained within the proximal end 56 of elongate member 14 through a frictional arrangement or relationship created between the proximal end 56 of elongate member 14 and the mounting ring 60 as will be further discussed hereinbelow. Mounting ring 60 assists in securing elongate member 14 to housing 12.

Preferred Process of Manufacture of Access Device

The preferred process or method of manufacture of access device 10 will now be discussed. Referring now to the flow chart (STEP 200) of FIG. 5, the first step of the process is to prepare elongate member 14. As mentioned hereinabove, elongate member 14 is preferably a tubular braid. Tubular braids suitable for use as an access device are commercially available from, e.g., textile manufacturers, and, in particular, textile manufacturers specializing in medical devices. Tubular braid is preferably cut to a desired length as dictated by the desired surgical objective for which device 10 will be used, illustrated as (STEP 210).

Figure 5:
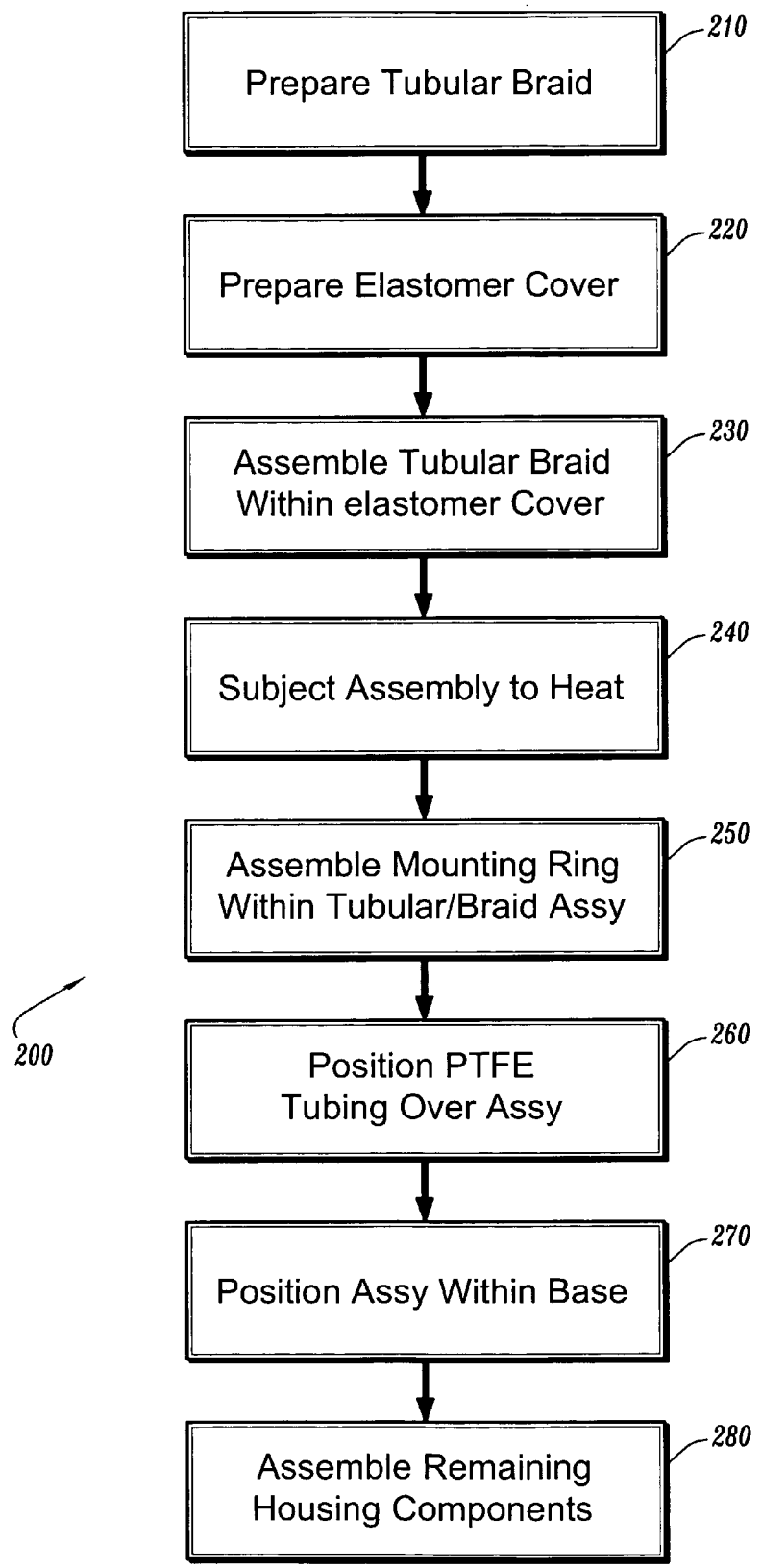
FIG. 5 is a flow chart depicting a preferred method of manufacture of the access apparatus in accordance with the further embodiment of the invention.
Figure 6:
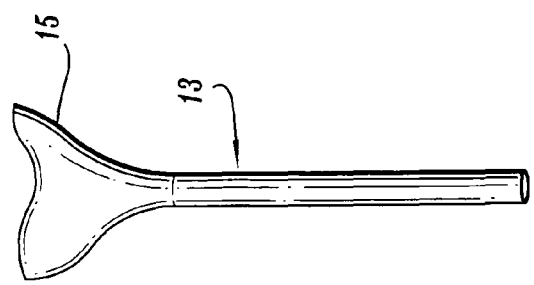
FIG. 6 is a view illustrating the elastomer cover of the access apparatus.

With continued reference to FIG. 5, an elastomer cover 13, preferably, a urethane cover is provided and cut to the desired length to correspond to the length of the tubular braid (STEP 220). FIG. 6 depicts a preferred arrangement of urethane cover 13. The urethane cover 13 preferably has a flared proximal portion 15 to define an inner diameter which increases toward the proximal end of the urethane cover 13. Such flaring of the end of urethane cover 13 may be effectuated by conventional extrusion processes used in forming the urethane cover 13. Preferably, the thickness of the material of the elastomer cover including the flared portion 15 is constant throughout its length. Thereafter, the tubular braid 17 is positioned within the urethane cover (STEP 230) to assemble the unit.

With elastomer cover 13 appropriately placed over the tubular braid, the assembly is subjected to a heating process (STEP 240) by positioning the assembly within an oven. In addition, pressure is applied by applying a vacuum, using a press or mold, so as to press the heated cover 13 into the braid. As a result of the heating process, the elastomer, e.g., urethane, becomes embedded within the fabric of the tubular braid to define a tubular braid/elastomer assembly. The assembly is thereafter cooled for a period of time.

Figure 7:
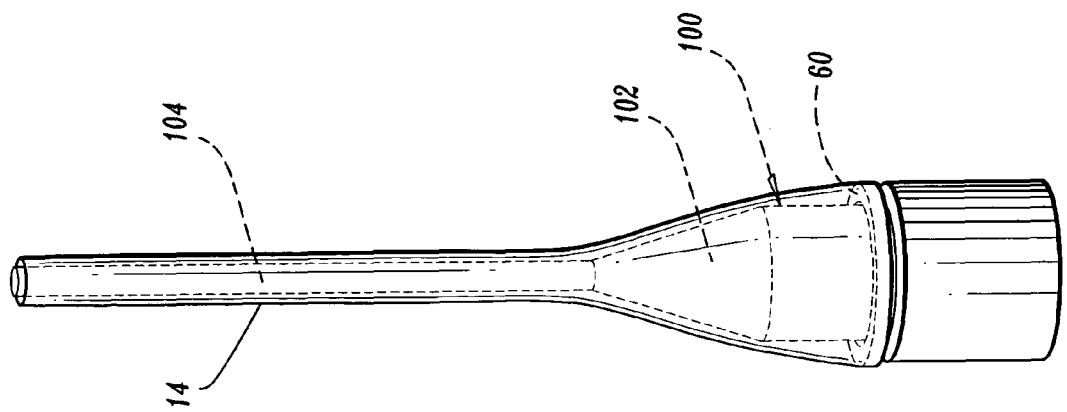
FIG. 7 is a view illustrating a building mandrel utilized for assembly of the access apparatus in accordance with the embodiment of FIG. 5.

The components of housing 12 and elongate member 14 are then assembled. In the preferred embodiment, a building or centering mandrel is utilized to assemble the components. A preferred mandrel is depicted in FIG. 7. This mandrel 100 includes a frusto-conical head 102 and a general rod-shaped element 104 extending from the head 102. Initially, mounting ring 60 is placed onto the mandrel 100. The elongate member 14 (comprising the tubular braid/elastomer assembly) is then slid over the mandrel 100 to a position where mounting ring 60 is received within the flared proximal end of the assembly as depicted in FIG. 7. (STEP 250) It is envisioned that the proximal end of the elongate member may stretch to an expanded position to receive mounting ring 60. In this arrangement, mounting ring 60 is preferably frictionally secured within the assembly 14 adjacent the proximal end. The elongate member 14 is then ground or cut at the distal end to the oblique surface 58a depicted in FIG. 1.

Figure 9:
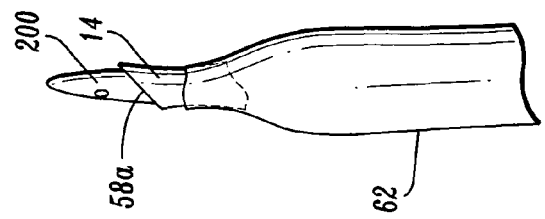
FIG. 9 is a view illustrating the distal end of the access apparatus with a needle positioned therein.
Figure 8:
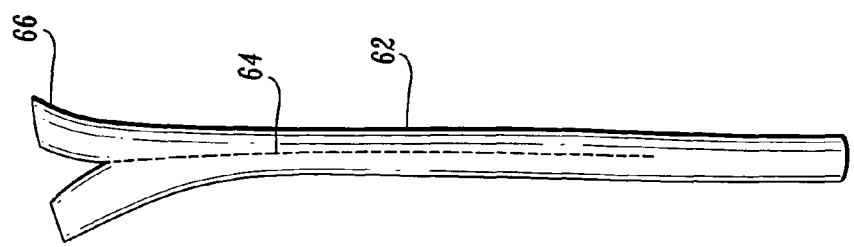
FIG. 8 is a view of PTFE tubing which is mounted over the access apparatus in accordance with the embodiment of FIGS. 1-4.

The elongate member 14 and mounting ring 60 are removed from the mandrel 100. At this point in the process, an outer plastic tubing, desirably PTFE tubing, may be placed onto the elongate member 14 (STEP 260). FIG. 8 depicts the preferred tubing. The proximal end 66 of the tubing 62 may be partially separated or weakened to facilitate its detachment. Alternatively, the PTFE tubing 62 may be scored along a score line 64 to facilitate detachment during use. The tubing 62 may be secured to the tubular braid/elastomer assembly adjacent its proximal end or mounting ring 60 with an adhesive or glue. Desirably, the tubing 62 extends beyond the oblique surface 58a, as shown in FIG. 9. FIG. 9 depicts the distal end of elongate member 14, with a needle 200 extending out of elongate member 14. The tubing 62 provides smooth transition from needle 200 and the oblique surface 58a. The needle 200 may be provided with the apparatus 10 as part of a kit or system for use during the surgical procedure.

With reference to FIGS. 3-4, in conjunction with FIG. 5, assembly is continued by positioning the tubular braid/elastomer assembly 14 within base 16 of housing 12 such that mounting ring 60 is positioned within the interior of the base 16 (STEP 270). Mounting ring 60 preferably causes tapered portion 32 of base 16 to deflect radially outwardly whereby, subsequent to positioning within the base 16, the mounting ring 60 engages transverse shelf 32c of the base 16. Thereafter, the assembly of housing 12 is continued (STEP 280). Hub 18 is assembled within base 16. In this position, annular wall 36 of hub 18 is received within mounting ring 60 of elongate member 14 and vertical locks 38 are received within recesses 26 of base 16. Thereafter, seal 18 is positioned within hub 16. Assembly is continued by mounting cover 22 to base 16 whereby shelf 54 of the cover 22 engages locking shelf 30 to secure the components. Outer circumferential wall 44 of seal 18 is accommodated within circumferential recess 52 of cover 22. Cover 22 secures the remaining components within base 16. It is envisioned that in the assembled condition mounting ring 60 may be pressed against the proximal end of elongate member 14 to compress the member 14 against tapered portion 32 of base 16. In addition, mounting ring 60 is prevented from release from base 16 by engagement with transverse shelf 32c of the base 16.

Use of the Apparatus

Figure 10:
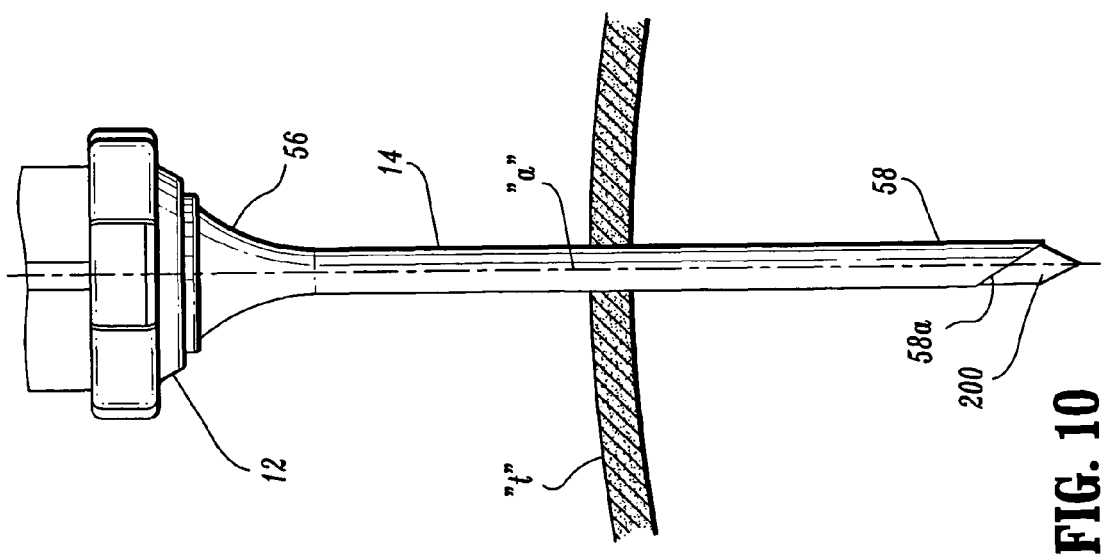
FIG. 10 is a cross-sectional view illustrating use of the access apparatus in accordance with the embodiment of FIGS. 1-4 to access a tissue site.

A method of use of the apparatus 10 will now be discussed. As depicted in FIG. 10, device 10 is percutaneously introduced to access a target site beneath the patient's skin. Preferably a needle or trocar 200 positioned in the device 10 to facilitate entry through the surgical site as discussed in connection with FIG. 9. It is noted that oblique end 58a of elongate member 14 facilitates passage of access device 10 within the tissue. The needle or trocar is thereafter withdrawn leaving access device 10 within the tissue. Desirably, a pneumoneedle is used for entry through the patient's skin and underlying layers and then used to introduce insufflation gas, in the case of laparoscopic surgery.

Figure 11:
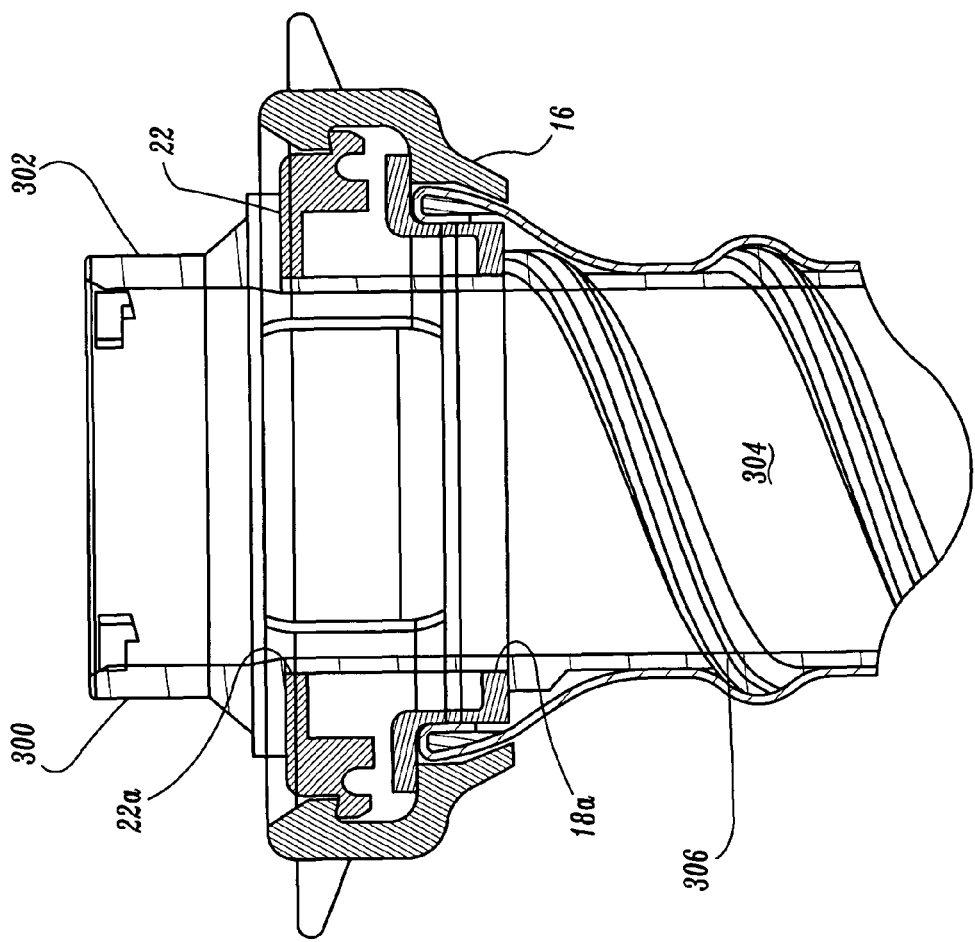
FIG. 11 is a cross-sectional view of a dilator for the access apparatus in accordance with the embodiment of FIGS. 1-4 and 7-8.

Referring to FIG. 11, a cannula 300 is then introduced within the inner lumen of the expandable elongate member 14 to expand the tubular braid/elastomer assembly to a desired internal diameter. The expansion of the elongate member 14 breaks the PTFE tubing 62. In the preferred embodiment, cannula 300 includes cannula housing 302 and a cannula sleeve 304 extending from the housing. Cannula sleeve 304 has an external threaded portion 306. The diameter of cannula sleeve 304 is greater than the internal diameter of elongate member 14. Cannula 300 is preferably rotated whereby the threaded portion 306 advances the cannula sleeve 304 within elongate member 14 of access device. The housing 12 desirably includes one or more flanges for engaging the threaded portion 306. In one embodiment, adjacent threads of threaded portion 306 engage flange 22a of cover 22 and flange 18a of hub 18 to advance cannula 300 upon rotation of the cannula 300, i.e., flanges 18a, 22a function as an internal thread structure which are engaged by threaded portion 306 to advance the cannula 300. Upon advancement, elongate member 14 expands to a second enlarged diameter shown in FIG. 11. The threaded portion enables the advancement of cannula 300 while minimizing the force directed in the distal direction. The threaded portion 306 may additionally be arranged for engaging the tissue.

Figure 12:
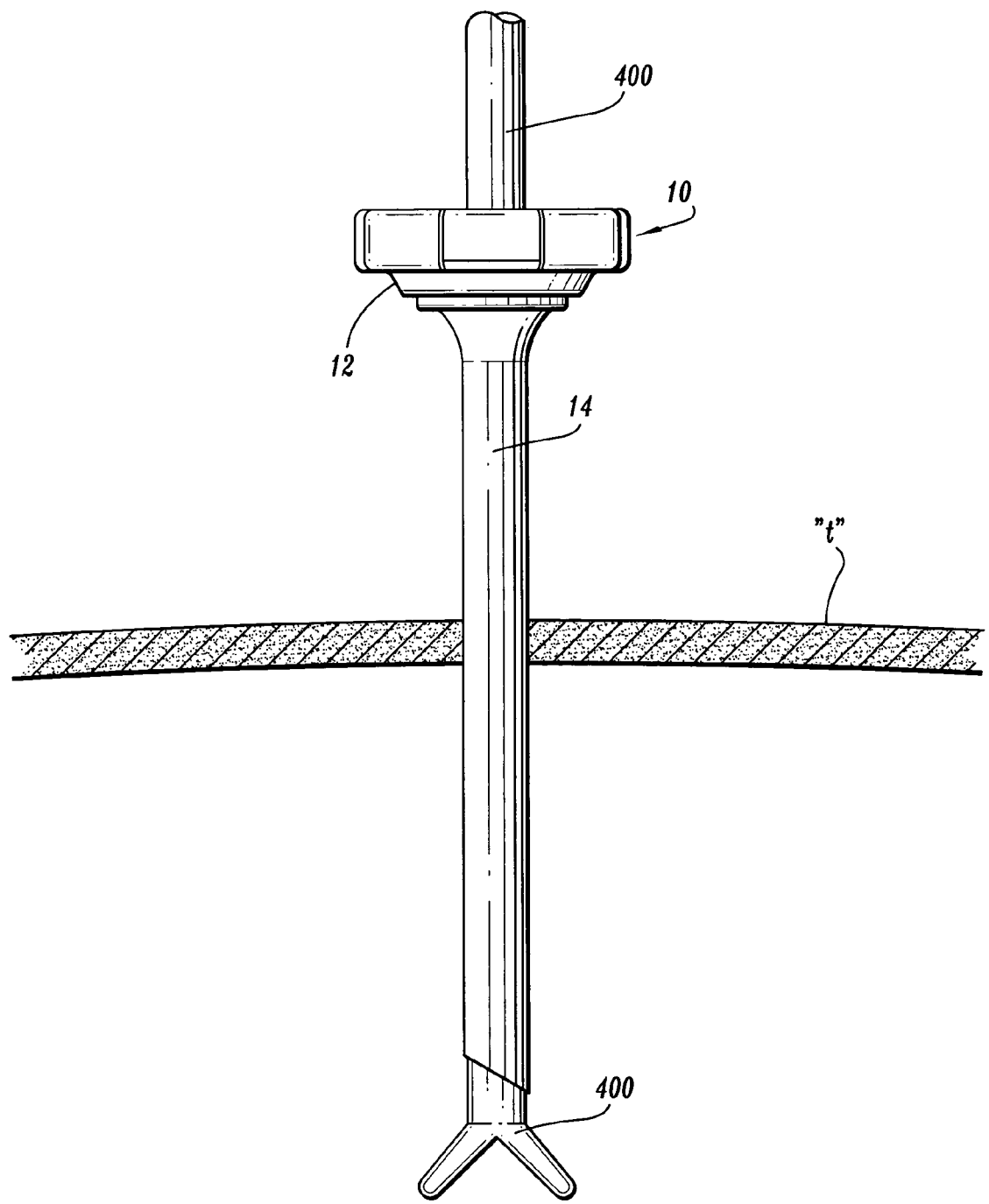
FIG. 12 is a cross-sectional view illustrating the use of the access apparatus in accordance with the embodiment of FIGS. 1-4 and 7-9.

It is envisioned that prior to insertion of cannula sleeve 304, elongate member 14 may be expanded with a dilator (not shown). It is also envisioned that the cannula sleeve 304 may be devoid of threads. Surgical instruments, scopes, etc. 400 may be introduced through the cannula to perform the desired procedure as shown in FIG. 12. After the procedure is finished, the cannula 300 is removed which causes tubular braid/elastomer assembly to collapse for subsequent removal. Optionally, other different diameter dilators or cannulas may be advanced within device 10 as desired.

It will be understood that various modifications may be made to the embodiments disclosed herein. For example, in a further embodiment, the base has a flange arranged for deflecting to receive the mounting ring 60, in a snap-fit manner so as to fixedly retain the ring 60. Although the ring depicted in the figures is round, the ring may have polygonal or oval shapes. Therefore, the above description should not be construed as limiting, but merely as exemplifications of preferred embodiments. Those skilled in the art will envision other modifications within the scope and spirit of the claims appended hereto.

What is claimed is:

1. A surgical access system, which comprises:
   a housing including an internal seal defining a passage therethrough, the housing defining a first internal thread segment proximal of the internal seal and a second internal thread segment distal of the internal seal, the housing including a base and a hub at least partially positionable within the base;
   a mounting element disposed between the base and the hub;
   a tubular member mounted to the housing, the tubular member comprising a braided material adapted to expand from a first initial condition having a first cross-sectional dimension to a second expanded condition having a second-cross sectional dimension greater than the first cross-sectional dimension, the tubular member having an axial lumen, wherein a proximal end of the tubular member is folded over the mounting element such that the proximal end of the tubular member is captured between the mounting element and the base, and between the mounting element and the hub, to thereby frictionally engage the tubular member to the housing; and
   a cannula positionable within the housing and the tubular member, the cannula including an external threaded portion, the external threaded portion engageable with the first and second internal thread segments of the housing whereby rotation of the cannula causes advancement thereof in a distal direction due to cooperative engagement of the external threaded portion and the first and second internal thread segments, the cannula dimensioned to radially expand the tubular member to cause the tubular member to assume the second expanded condition.

2. The surgical access system according to claim 1 wherein the distal end of the tubular member defines an oblique end surface.

3. The surgical access system according to claim 1 wherein the mounting element is substantially annular in configuration.

4. The surgical access system according to claim 1 wherein the internal seal is adapted to establish a substantial sealed relationship with the cannula.

5. The surgical access system according to claim 1 wherein the hub includes a wall extending within the tubular member, the wall having an internal flange, the internal flange being the second internal thread segment.

6. The surgical access system according to claim 1 wherein the housing includes a cover at least partially positionable in the base, the cover including an internal flange, the internal flange being the first internal thread segment.

7. The surgical access system according to claim 1, wherein the mounting element includes at least a first and second substantially planar surface.

8. The surgical access system according to claim 7, wherein the tubular member engages the at least first and second substantially planar surfaces of the mounting element.

9. The surgical access system according to claim 1, wherein the hub includes a wall extending within the axial lumen of the tubular member.

10. The surgical access system according to claim 1 wherein the mounting element is dimensioned to frictionally engage an internal wall portion of the tubular member.

11. The surgical access system according to claim 10 wherein the base includes a transverse shelf whereby the mounting element is retained within the housing through operative engagement with the transverse shelf of the base.

12. The surgical access system according to claim 10 wherein the seal element is mounted within the base, wherein the seal element defines an aperture for sealed reception of an elongate object.

* * * * *